United States Patent [19]

Block et al.

[11] 4,064,229

[45] Dec. 20, 1977

[54] DENTAL PLAQUE DISCLOSING AGENT

[76] Inventors: Philip L. Block, 416 Deerfield Drive, Moraga, Calif. 94556; John P. Derdivanis, 6284 Crown Ave., Oakland, Calif. 94600

[21] Appl. No.: 701,921

[22] Filed: July 1, 1976

Related U.S. Application Data

[60] Continuation of Ser. No. 584,224, June 5, 1975, Pat. No. 3,997,658, which is a continuation of Ser. No. 343,764, March 22, 1973, abandoned, which is a division of Ser. No. 109,054, Jan. 22, 1971, Pat. No. 3,723,613.

[51] Int. Cl.$^2$ ............... A61K 29/00; G01N 21/02; G01N 21/16
[52] U.S. Cl. ........................... 424/7; 424/9; 424/45; 424/49
[58] Field of Search ............... 424/3, 7, 9, 49

[56] References Cited

U.S. PATENT DOCUMENTS 2,151,495  3/1939  Bender .................................. 424/7

FOREIGN PATENT DOCUMENTS 423,858  2/1935  United Kingdom .................. 424/7

OTHER PUBLICATIONS

Caldwell, J. Dentres, vol. 48, Sept.-Oct. 1969, pp. 913-915.
Color Index 2nd Ed., 1956, pp. 1133, 1791, 1793, 3348, 3349, 3351, 3357, 3391, 3392.
Conn., Biol. Stains, Stain Comm., Biotech Pub. 5th ed., 1946, pp. 117-121, 292-298.

Primary Examiner—Albert T. Meyers
Assistant Examiner—A. P. Fagelson
Attorney, Agent, or Firm—Townsend and Townsend

[57] ABSTRACT

Disclosing agents for use in control of dental plague. The agents are compositions comprises of FDC Red No. 3 and FDC Blue No. 1; FDC Red No. 3 and FDC Green No. 3 and FDC Red No. 3 and Hercules Green Shade 3.

2 Claims, No Drawings

DENTAL PLAQUE DISCLOSING AGENT

This is a continuation of application Ser No. 584,224, filed June 5, 1975, now U.S. Pat. No. 3,997,658, which is a continuation of application Ser. No. 343,764, filed Mar. 22, 1973, now abandoned, which is a divisional application of Ser. No. 109,059, filed Jan. 22. 1971, now U.S. Pat. No. 3,723,613.

This invention relates to novel disclosing agents for use in the improvement of oral hygiene practices. More specifically the invention pertains to combinations of dyes; FDC Red No. 3 and FDC Blue No. 1; FDC Red No. 3 and FDC Green No. 3; FDC Red No. 3 and Hercules Green Shade 3 for employment as disclosing agents in the control of dental plaque.

Dental Plaque is a well-organized structure which forms on tooth surfaces and restorations. It consists mainly of bacteria surrounded by a matrix derived primarily from saliva and the bacteria themselves. Plaque differs from other soft tooth deposits such as materia alba and food debris in that it has a definite architecture and cannot be flushed away by rinsing with water.

It is well established that dental plaque plays a major role in the etiology of periodontal diseases and caries. Although the exact manner in which plaque contributes to these disease states is not known at present, it is appreciated that effective and thorough removal of these deposits is absolutely essential for oral health. Accordingly it is desirable that an effective plaque control program be established as part of the treatment plan for every dental patient. For this program to be effective the patient must be motivated to carry out thorough daily plaque control techniques. Motivation can be achieved, however, only by establishing goals that are meaningful and attainable by the patient. Experience has shown that most patients would not be sufficiently motivated to practice good oral hygiene if they were simply told that plaque is a bacterial colony growing on their teeth; that plaque produces gingival disease and caries and must be removed daily. However, the entire concept of what plaque is and what it does to tissue can be made vital and important to the patient by "visualization" whereby every patient is shown his plaque in situ and under the phase contrast microscope. The patient may also observe the diseased gingival areas and their juxtaposition to the places of plaque accumulation. These visual demonstrations serve two main purposes. First, it shows the patient that he does indeed have these dangerous bacterial deposits called plaques on his teeth. Secondly, by microscopic visualization, he sees that those innocent looking masses are composed of millions of living bacteria of differing shapes; some even having the ability to move about. Experience has shown that the technique of visualization of plaque generates in patients a true interest in plaque, and an obvious and apparent concern for its prompt removal.

Since plaque is translucent or tooth-colored, it is necessary that it be appropriately stained in order for it to be made visible. Disclosing dyes have been in use for over 50 years. Many substances have been used, e.g. iodine, basic fuchsin neutral red, etc. Some dyes previously tried by the prior art could not be used because they were suspected carcinogens, others appeared in the urine, and taste was a drawback to many materials.

Since its development in 1963, a disclosing tablet containing FDC No. 3 as the staining agent has been widely employed as a disclosing agent to stain plaque. One of the reasons the dye was so widely accepted was because it met the criteria established at that time for an effective disclosing medium; namely, that it should have a pleasing shade of red. However, with regular use of the FDC Red No. 3 tablet, it became abundantly clear that the "pleasing shade of red" adversely affected the utility of the wafer. The plaque interproximally and at the gingival margin, especially in the posterior areas, could not easily be seen because of poor contrast between the gingiva and the stained plaque. Accordingly, the use of a red disclosing dye reveals that red is the wrong color since plaque that has been stained red is extremely difficult to see due to poor contrast with the oral tissues, especially in the back areas of the mouth and between the teeth. It should be noted that it is these precise areas which are the most prevalent sites of caries and periodontal disease.

A disclosing agent having all the desirable properties of the current red media, but possessing, however, a color which would be in sharp contrast to the gingival tissues would vastly improve the effectiveness of such a product. The continuing search for an improved disclosing dye preparation has led to the development of the blue dye medium of the invention which provides a two-tone dye test for dental plaque.

The novel dyes of the invention not only stain plaque a color which contrasts well with the tissues and teeth, thus making plaque visible even in the hard to see places, but they possess the property of selective differential staining and thereby permit a distinction to be made between areas of old thick accumulations and thin recent deposits. It has been well documented in dental literature that it is thick plaque deposits which are generally associated with periodontal disease and exhibit the anaerobic flora seen in periodontal pockets. In other words, thick old plaques are probably more pathogenic than the new deposits.

The novel dyes of the invention are unique in that by color alone the third dimension of plaque, its age and thickness, can be readily estimated. Thick plaques stain blue and thin plaques stain red. Since old and new plaques have their own characteristic microbial morphology, the bacterial types can be also judged by color differentiation using the dyes of the invention. Utilizing the novel two-tone dye test for dental plaque the patient can, for the first time, judge for himself whether he has been practicing effective plaque removal by noting whether any plaque deposits which may be stained are either red or blue. If he consistently misses certain areas they will be considerably thicker and therefore stained blue. If he has been doing a thorough and effective job of plaque control, he will either show no stain pickup or if he has thin deposits they will stain red.

The dentist can also use this dye test to obtain virtually a quantitative evaluation of the effectiveness of the patients plaque control.

Additionally, the dyes are a useful tool in dental research. For the first time the extremely important third dimension of plaque, its thickness can be noted by color differential and this information recorded in a photograph. Studies that have been conducted heretofore to evaluate the effectiveness of antiplaque agents and oral hygiene aids using the prior art erythrosine have failed to convey the information about plaque thickness.

In the following study patients were selected at random and their teeth were stained with a representative dye of the invention (FDC Red No. 3 and FDC Green No. 3). Kodachromes were taken of these stained areas from which plaque was to be removed for microscopic examination. At all times plaque samples were taken from teeth that showed red and blue plaque on the same tooth. This was done to eliminate any variation in plaque bacterial morphology that could exist between one tooth and another. Each plaque colony was disected with the tip of a fine curette. The samples were placed on a slide, suspended in Ringers Solution, and examined and photographed through a phase contrast microscope at 400 X and 1000 X. According to the invention it is now possible to distinguish between old thick plaque and new thin plaque based on the distinctive color each takes with the novel dye of the invention.

Generally, blue plaque shows the following clinical and microscopic features:
1. Considerably greater thickness than red plaque.
2. High degree of architectural organization. Cocci, rods and/or filaments arranged in parallel rows forming fan-shaped patterns. These rays were perpendicular to the tooth but this pattern was broken at the time of sample removal.
3. Filaments intertwined forming a mesh work.
4. Motility — present in some blue plaques.
5. Spiral organisms and vibrios.

Red plaques are distinguished by the following:
1. Extreme thinness — to the extent that sometimes it was hard to obtain sufficient material for examination.
2. Low density of organisms.
3. No evidence of any orderly architecture.
4. No motility.
5. No filaments, spiral organisms or vibrios.

On some teeth treated with the dye it was also possible to distinguish an intermediate zone between the red and blue areas that had a definite purple color. This intermediate area tended to look more like blue plaque than red plaque but the thickness of this plaque was less than that of blue plaque.

Close examination of the Kodachromes revealed some interesting facts. Plaque colonies growing on a tooth surface displayed a central raised blue mass surrounded by a red and/or purple peripheral zone which was lower than the central mass. The red zones of adjacent colonies tended to fuse forming red fields peppered with blue raised areas. Those tooth surfaces that were not covered with plaque did not show the dye at all. It should be noted that patients treated with the dye do not find the blue color objectionable or the taste unpalatable. The blue color fades quickly from teeth, restorations and tissues with simple water rinses and brushing. In addition, stains are easily removed from laundry or plumbing fixtures.

The dyes of the invention find particular value as research and diagnostic tools. They can be used in evaluating antiplaque agents, or plaque control techniques and devices by providing vital information about the third dimension of plaque, its thickness. Prior art disclosing dyes have not been able to supply this information, thus severely limiting the value of those studies conducted to measure the effectiveness of plaque removal.

The relative ratio of one dye to the other in formulating the dye compositions of the invention is not critical and the unobvious two-tone properties may be achieved by employing for each part by weight of FDC Red No. 3 from about .1 to about 4 parts by weight of either FDC Green No. 3, FDC Blue No. 1 or Hercules Green Shade 3. A preferred ratio would involve one to two parts by weight of the latter for each part by weight of FDC Red No. 3.

Where the dye is to be used in the form of a solution, the concentration of the dye is not critical and may vary from about 600 to 1200 mg. per 100 ml. of solution. If one desires to utilize the dyes as tablets or wafers, the amount of dye included in each tablet or wafer is not critical and may vary from about 20 mg. to about 100 mg. per dosage unit.

A representative example of a combination of FDC Red No. 3 and FDC Green No. 3 that may be used in the practice of the invention is as follows:

| | | |
|---|---|---|
| FDC Red No. 3 | 200 | mg. |
| FDC Green No. 3 | 400 | mg. |
| Surfactant (Tween 20) | 0.1 | ml. |
| Tap water | 60 | ml. |

The formulation is painted on the teeth and gingiva, retained a few seconds and rinsed off with a small amount of water. Newly formed plaque stains red whereas old plaque stains deep blue or purple.

The manner by which the dye is made available to the mouth area is not critical and will vary according to patient acceptance and convenience. For example, in addition to painting on the teeth the novel dye can be formulated as a chewable tablet, wafer, powder, lozenges, aerosol, liquid concentrate, etc.

Examples directed to the preparation of such formulations are as follows:

| Chewable Tablets or Wafers | Grams |
|---|---|
| Mannitol, granular | .905 |
| Flavoring oils, spray dried in gum acacia | .025 |
| Calcium stearate | .010 |
| FDC Red No. 3 | .020 |
| FDC Green No. 3 | .040 |
| | 1.000 |
| Lactose, spray dried | .855 |
| Flavoring oils, spray dried in gelatin | .020 |
| Magnesium stearate | .014 |
| FDC Red No. 3 | .020 |
| FDC Green No. 3 | .040 |
| Saccharin | .001 |
| Citric acid | .050 |
| | 1.000 |

| Fluid Preparation (May be painted on full strength, or diluted with water for use as a rinse | % by weight |
|---|---|
| Ethanol, USP | 15.00 |
| Polysorbate 80 | 0.20 |
| Flavoring oils | 0.50 |
| Glycerin | 5.00 |
| FDC Red No. 3 | .25 |
| FDC Blue No. 1 | .50 |
| Water, q.s. ad | 100.00 |

| Aerosol Sprays | % by weight |
|---|---|
| Glycerin | 15.0 |
| Ethanol, absolute | 43.4 |
| Saccharin | 0.1 |
| Flavor | 0.2 |
| Propellant 12 | 16.0 |
| Propellant 114 | 25.0 |
| FDC Red No. 3 | 0.1 |
| FDC Green No. 3 | 0.2 |
| | 100.0 |
| Ethanol, USP | 20.00 |
| Glycerin | 5.00 |
| Flavoring oils | 0.35 |
| FDC Red No. 3 | 0.25 |
| FDC Green No. 3 | 0.50 |
| Water | 68.90 |
| Propellant 12 | 5.00 |
| | 100.00 |

-continued

| Lozenges | Grams |
| --- | --- |
| Corn syrup solids, spray dried | .880 |
| Flavoring oils, spray dried with modified starch | .050 |
| Calcium stearate | .010 |
| FDC Red No. 3 | .020 |
| Hercules Green Shade 3 | .040 |
| | 1.000 |

What is claimed is:

1. A composition in the form of an aqueous solution, for application to the oral cavity to accomplish the differential disclosure of dental plaque, said composition consisting essentially of FDC Red No. 3 and FDC Blue No. 1, said Blue No. 1 being present in an amount from about 0.1 to 4 parts by weight per each part by weight of FDC Red No. 3, said composition differentially staining areas of old, thick accumulations of dental plaque blue and thin, recent deposits of dental plaque red, whereby effectively practiced plaque removal on a given tooth shows, and can be photographed, as either no stain pickup or thin deposits staining red, while certain areas on said tooth if consistently missed, will be considerably thicker and therefore stained blue, and on some teeth, an intermediate definite purple zone can be distinguished between the red and blue areas, said intermediate definite purple area tending to look more like blue plaque than red plaque, but the thickness of this purple plaque being less than that of blue plaque, while tooth surfaces not covered with plaque do not show the dye at all.

2. The composition of claim 1 wherein the composition includes a surfactant.

* * * * *